United States Patent [19]

Sinnott et al.

[11] Patent Number: 4,826,211

[45] Date of Patent: May 2, 1989

[54] GREETING CARD

[75] Inventors: Michael J. Sinnott, 52 Lincoln Street, Stones Corner, Queensland; Adrian J. McCullagh, Stones Corner, both of Australia

[73] Assignee: Michael J. Sinnott, Queensland, Australia

[21] Appl. No.: 76,757

[22] Filed: Jul. 23, 1987

[51] Int. Cl.$^4$ ...................... B42D 15/00; B42D 15/02; A44C 3/00; A61F 13/02

[52] U.S. Cl. ...................................... 283/117; 40/299; 229/92.8; 428/40

[58] Field of Search ..................... 283/1 R, 100, 90 R, 283/101, 103; 273/157 R, 139; 434/363, 364; 229/92.8; 40/2 R; 281/18; 428/40

[56] References Cited

U.S. PATENT DOCUMENTS

| | | | |
|---|---|---|---|
| 3,141,549 | 7/1964 | Koehler | 229/92.8 |
| 3,329,333 | 7/1967 | Ormond | 229/92.8 |
| 3,822,901 | 7/1974 | Seidman . | |
| 4,145,731 | 3/1979 | Adamich | 229/92.8 |
| 4,200,222 | 4/1980 | Feuer | 229/92.8 |
| 4,203,620 | 5/1980 | Long | 229/92.8 |
| 4,278,199 | 7/1981 | Tanaka | 229/92.8 |
| 4,500,021 | 2/1985 | Bildusas | 428/40 |
| 4,512,581 | 4/1985 | Levine . | |
| 4,613,157 | 9/1986 | Drabish | 283/1 R |

FOREIGN PATENT DOCUMENTS

| | | | |
|---|---|---|---|
| 772046 | 11/1967 | Canada | 283/100 |

*Primary Examiner*—Frank T. Yost
*Assistant Examiner*—Paul M. Heyranna. Sr.
*Attorney, Agent, or Firm*—Foley & Lardner, Schwartz, Jeffery, Schwaab, Mack, Blumenthal & Evans

[57] ABSTRACT

The invention comprises a greeting card having first and second hingedly connected sheets with indicia thereon in conventional format, with the addition of a third hinged sheet juxtaposed with the second sheet and in sealed relationship thereto. The third sheet is sealed to the second sheet around their free edges, and contains further indicia which is not normally visible, and is revealed only by irreversibly destroying the integrity of the seal between the second and third sheets. In another embodiment of the invention, the third sheet is detachably attached to the second sheet so that it may be detached and affixed repetitively.

7 Claims, 3 Drawing Sheets

GREETING CARD

BACKGROUND OF FIELD OF THE INVENTION

This invention relates to a greeting card. In praticular, the invention relates to a greeting card wherein at least part of the greeting or message thereon is hidden from view.

There are many different types of greeting cards for different events or occasions, for example birthday cards, congratulatory cards, "get well" cards, post cards, etc. The sender normally selects a card from a variety of cards having different designs and messages or greetings and then forwards the selected card to the addressee. Such card sending is commonplace and the receipt of a conventional greeting card is often taken for granted by the addressee. That is, the card may not elicit a response from the addressee. To personalise the exercise of card giving, the card sender often picks a card having a distinictive message or greeting thereon or one which the sender considers would appeal to the receiver.

Novelty greeting cards also have been devised to enliven the sending of messages. Such novelty cards include musical cards, illuminated cards and pop-up cards.

One type of novelty greeting card contains a so-called "hidden message". For example, U.S. Pat. No. 4,512,581 teaches a greeting card which has a message hidden in a crossword puzzle-type lattice. By solving the crossword, the receiver is able to learn the message. However, the message is known to the sender since it is written on a detachable sheet attached to the card when purchased. U.S. Pat. No. 3,822,901 describes another form of hidden message apparatus which comprises an element having a message thereon hidden under a removable opaque layer. The element is typically a tab, sticker or tag which can be affixed to an envelope to seal it. By scratching off the opaque layer, the receiver is able to learn of the message. Again, the message is not hidden to the sender since it is written on a second element releasably coupled to the first element.

SUMMARY OF THE INVENTION

It is an object of the present invention to provide an improved novelty greeting card which introduces an extra factor or dimension into the custom of sending greeting cards, by keeping the message or greeting hidden from the sender as well. That is, at least part of the message or greeting on the card is not able to be read by the sender when the card is purchased. There is therefore a risk factor or an unknown factor in the selection and forwarding of the greeting card.

In one broad form, the present invention provides a greeting card comprising first and second hingedly-connected sheets, said first and/or second sheet(s) having indicia thereon, characterised in that said greeting card comprises a third sheet having further indicia thereon which relates to the indicia on said first and/or second sheet(s), said third sheet being juxtaposed with said second sheet and in sealed relationship thereto such that said further indicia is not visible, wherein said further indicia is revealed only by irreversibly destroying the integrity of the seal between said second and third sheets.

A particular advantage of the greeting card of the present invention is that the hidden message can act as a catalyst for two-way communication between the sender and the receiver. That is, the receiver on learning the hidden message, will contact the sender to convey that information back to the receiver. Alternatively, the sender may contact the receiver to learn of the message. This will then provide a talking point to enable a dialogue to be commenced.

The "unknown" message adds a sense of adventure to the custom of sending greeting cards by requiring the sender to gamble on the hidden message being appropriate and appreciated. However, the sender has an inherent excuse for any card which is not appreciated, namely the sender can disclaim responsibility by pointing out that he was unaware of the message or greeting and the card was picked by chance. The sender can pass the responsibility on to the manufacturer of the greeting card.

In a preferred embodiment, the greeting card comprises a card of conventional design having a message or greeting thereon, with a further sheet being joined to the back of the card along all four borders. The further sheet contains a message or greeting which typically is a continuation of the conventional message in the greeting card. However, the message or greeting on the further sheet is not visible and cannot be learned without breaking the join between the further sheet and the rest of the card. In other words, a sender cannot learn of the message without irreversibly damaging the card.

The further sheet may be attached to the back of the card by any suitable known method. For example, the border of the further sheet may be glued to the card. Alternatively, the further sheet may comprise tabs which fold over the edges of the last sheet in the conventional card and are glued thereto. Preferably, all sheets of the card, including the further sheet, are hingedly-connected about a common axis.

In another form of the invention, the greeting card comprises a further sheet having a "hidden" message thereon, the further sheet being detachably affixed to a card of conventional design. The card contains a conventional message or greeting, but a "secret" or more intimate message may be written on the detachably affixed further sheet. This embodiment of the invention enables the sender to write a message on the first portion of the greeting card which may be read by others, as well as a more intimate or private message on the further sheet. By custom or convention, the message written on the further sheet is to be read only by the actual addressee. The addressee is able to display the card to others, knowing that the private or intimate message written on the further sheet remains confidential.

In the preferred embodiment, the further sheet is detachably affixed to a conventional form of greeting card by a weak restickable adhesive of known type. However, any other known suitable means of detachably affixing the further sheet to the greeting card can be used.

Further features and advantages of the invention will be apparent from the following detailed description of preferred embodiments thereof which are illustrated schematically in the accompanying drawings.

DETAILED DESCRIPTION OF PREFERRED EMBODIMENTS

Figure 1:
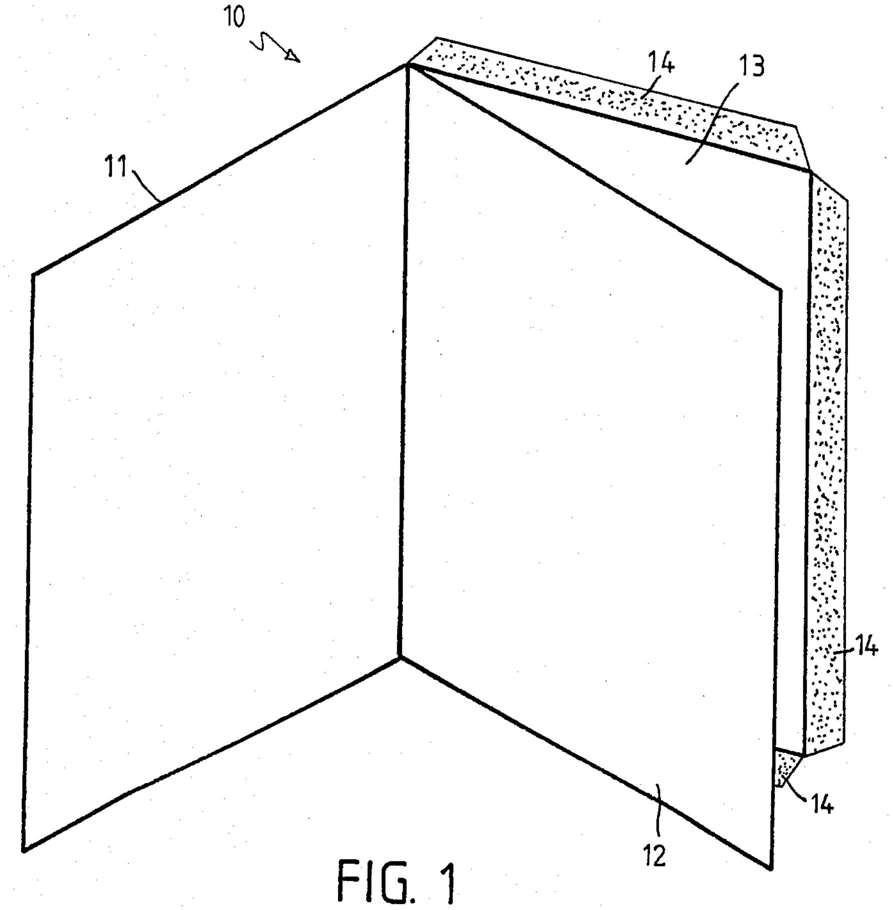
FIG. 1 is an exploded view of a greeting card of a first embodiment of the invention.

As shown in FIGS. 1 to 4, the greeting card 10 of the first embodiment comprises a pair of hingedly-connected sheets 11, 12, suitably made of stiffened paper or cardboard. The card 10 also comprises a third sheet 13 which is hingedly-connected to sheets 11, 12 about the same axis. A conventional message or greeting is written on either or both of sheets 11 and 12. However, a "hidden" or "secret" message is written on the third sheet 13. The third sheet 13 has tab portions 14 extending along its free edges. Preferably, the tab portions 14 are coated with an adhesive. During manufacture, the sheet 12 and sheet 13 are juxtaposed, the tab portions 14 are folded over the edges of sheet 12 and glued to sheet 12 so that the sheet 13 is sealed to sheet 12. In this manner, the message written on sheet 13 is not visible or discernable.

Figure 2:
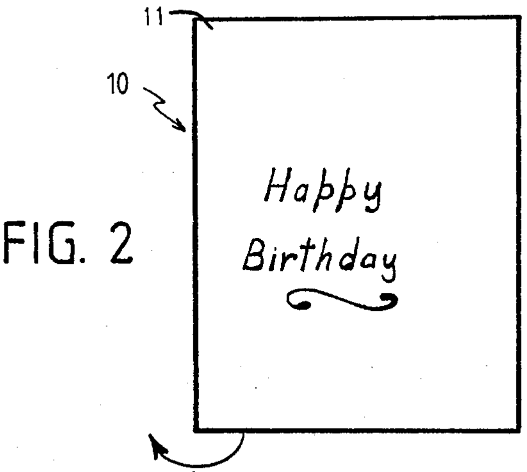
FIG. 2 illustrates the card of FIG. 1 in its folded state.
Figure 3:
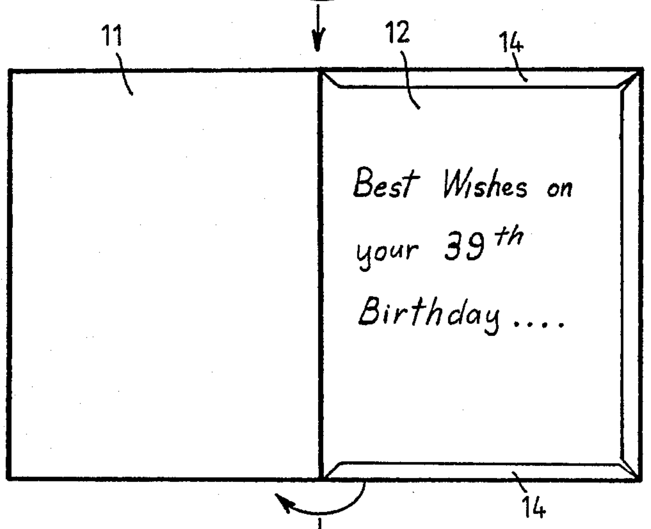
FIG. 3 illustrates the card of FIG. 1 in its conventional open state.
Figure 4:
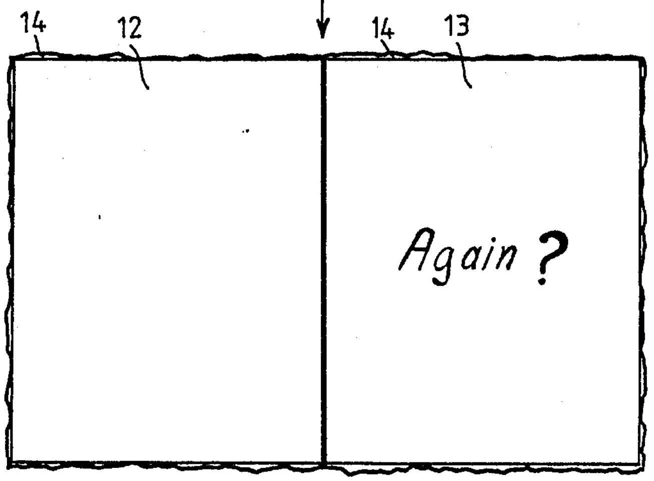
FIG. 4 ilustrates the card of FIG. 1 when opened to reveal the hidden message.

In a typical application of the invention, the greeting card will bear a general greeting on the cover sheet 11 as shown in FIG. 2. When the card is opened, as shown in FIG. 3, a conventional message on the inside of either or both of sheets 11 and 12 will be displayed to the reader. However, the message on the third sheet 13 cannot be read unless the seal between the second and third sheets is broken, for example by cutting through the tab portions 14 to thereby reveal the hidden message on the third sheet 13 as shown in FIG. 4.

Once the integrity of the seal between the second and third sheets has been broken, the sheets cannot be resealed. Thus, it is relatively easy to determine whether a card displayed for sale has been tampered with. Furthermore, the receiver will be able to ascertain whether the sealed section of the card has been opened by the sender (as such action would be contrary to the spirit or intent of the exercise).

Although the greeting card of the present invention is particularly suitable for humorous cards, its use is not limited thereto. The cards can be used as Valentine cards, for example to send particularly romantic or private hidden messages.

Alternative means for sealing the third sheet 13 to the second sheet 12 can also be used. For example, the third sheet may simply be glued around its border to the back of the second sheet 12, or the two sheets may be heat-sealed.

Preferably, the message written on the third sheet 13 is a continuation of the conventional message on the first and/or second sheets 11, 12, or at least has some relation thereto. For example, the message on the third sheet may be the punch line of a joke on the first and/or second sheets.

Figure 5:
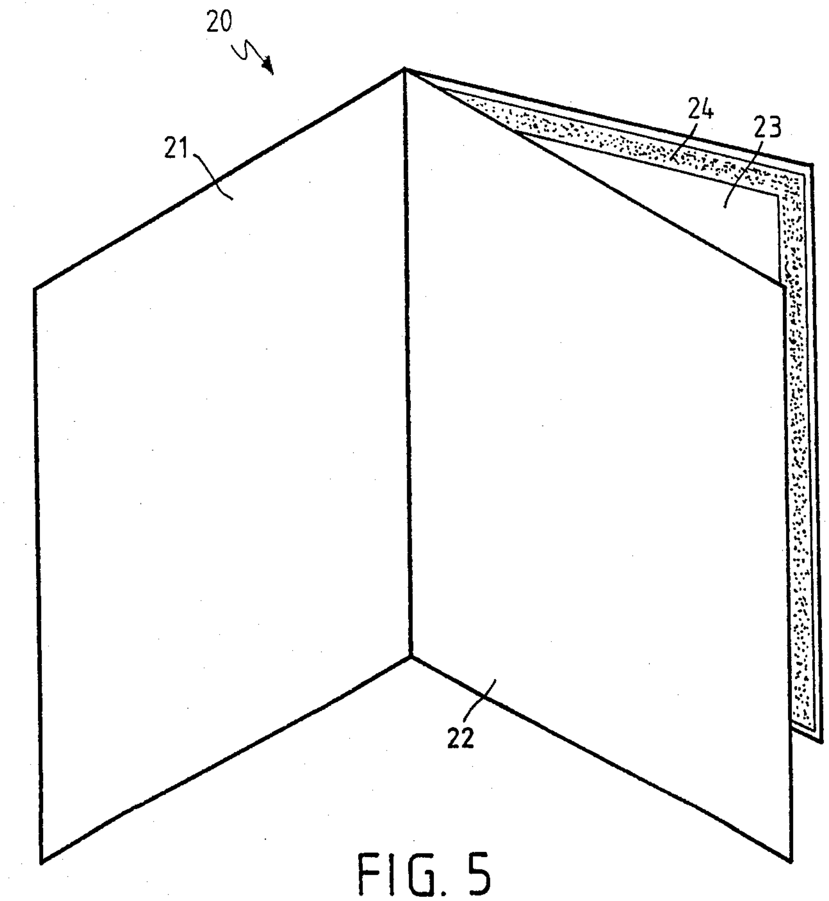
FIG. 5 is a perspective view of a greeting card according to another embodiment of the invention.

In another embodiment of the invention, illustrated in FIG. 5, a greeting card 20 comprises a pair of hingedly-connected sheets 21, 22 of conventional design. A third sheet 23 is detachably affixed to the second sheet 22 by means of a weak reusable adhesive 24 arranged about the periphery of sheet 23. In this manner, the sheet 23 is restickable to the back of sheet 22.

In this embodiment, the "hidden" message on the third sheet 23 may be written or read by the sender before forwarding the greeting card, without damaging the card. The card may also be displayed to others but, by convention or custom, the hidden or secret message on the third sheet is to be read only by the sender and/or receiver. Such a card is then able to be displayed with other cards, for example at Christmas time, without necessarily revealing the greeting or message on the third sheet which may be of a private nature.

The adhesive 24 is preferably a weal reusable adhesive which enables the third sheet 23 to be peeled off the back of sheet 22 and resealed repetitively. However, any other known suitable means for detachably affixing the sheet 23 to sheet 22 can be used.

The foregoing describes only some embodiments of the invention, and modifications which are obvious to those skilled in the art may be made thereto without departing from the scope of the invention as defined in the following claims.

We claim:

1. A greeting card comprising first and second hingedly-connected sheets, said first and/or second sheet(s) having indicia thereon, characterized in that said greeting card comprises a third sheet connected to said second sheet and having further indicia thereon which relates to the indicia on said first and/or second sheet(s), said third sheet being juxtaposed with said second sheet, the free edges of said second and third sheets being in sealed relationship such that said further indicia is not visible, wherein said further indicia is revealed only by irreversibly destroying the integrity of the seal between said second and third sheets.

2. A greeting card as claimed in claim 1, wherein said second and third sheets are joined by adhesive adjacent their free edges.

3. A greeting card as claimed in claim 1, wherein said third sheet comprises tab portions extending along its free edges, said tab portions being folded over corresponding free edges of said second sheet and affixed thereto.

4. A greeting card as claimed in claim 2 wherein said indicia comprises a message or greeting and said further indicia is a continuation of the message or greeting.

5. A greeting card comprising first and second hingedly-connected sheets, said first and/or second sheet(s) having indicia thereon, characterized in that said greeting card comprises a third sheet connected to said second sheet and having further indicia there on which relates to the indicia on said first and/or second sheet(s), said third sheet being juxtaposed with said second sheet and being detachably attached thereto, wherein said third sheet may be detached and affixed to said second sheet repetitively.

6. A greeting card as claimed in claim 5, wherein a strip of restickable adhesive material is provided at least partially around the periphery of said second and/or third sheet(s).

7. A greeting card as claimed in claim 6, wherein said indicia comprises a message or greeting and said further indicia is a continuation of the message or greeting.

* * * * *